United States Patent
Dominguez

(10) Patent No.: US 6,560,473 B2
(45) Date of Patent: May 6, 2003

(54) DISPOSABLE ECG CHEST ELECTRODE TEMPLATE WITH BUILT-IN DEFIBRILLATION ELECTRODES

(76) Inventor: Steven Dominguez, 19 Bridington, Laguna Niguel, CA (US) 92677

( * ) Notice: Subject to any disclaimer, the term of this patent is extended or adjusted under 35 U.S.C. 154(b) by 0 days.

(21) Appl. No.: 09/798,762

(22) Filed: Mar. 2, 2001

(65) Prior Publication Data

US 2002/0123679 A1 Sep. 5, 2002

(51) Int. Cl.[7] .......................... A61B 5/0408; A61H 1/04
(52) U.S. Cl. .................. 600/382; 600/386; 600/391; 600/393; 607/142
(58) Field of Search ................. 600/382, 386, 600/388, 389, 390, 391, 392, 393; 607/142

(56) References Cited

U.S. PATENT DOCUMENTS

| | | | |
|---|---|---|---|
| 5,078,134 A | * | 1/1992 | Heilman et al. ............. 607/142 |
| 5,184,620 A | | 2/1993 | Cudahy et al. |
| 5,733,324 A | | 3/1998 | Ferrari |
| 5,865,741 A | | 2/1999 | Kelly et al. |
| 5,938,597 A | | 8/1999 | Stratbucker |
| 5,995,861 A | | 11/1999 | Price |
| 6,065,154 A | * | 5/2000 | Hulings et al. ............. 600/393 |
| 6,173,198 B1 | * | 1/2001 | Schulze et al. ............. 600/393 |
| 6,259,939 B1 | * | 7/2001 | Rogel .......................... 600/390 |
| 6,400,975 B1 | * | 6/2002 | McFee ........................ 600/393 |
| 2001/0027270 A1 | * | 10/2001 | Stratbucker ................. 600/393 |

* cited by examiner

Primary Examiner—Lee Cohen

(57) ABSTRACT

A disposal ECG Chest Electrode Template with built-in defibrillation electrodes has a location tab so that the template can be easily, quickly and correctly placed on the patient's chest during emergency situations. The template and its electrodes is transparent to x-ray allowing it to remain on the patient's chest throughout x-ray diagnosis and evaluation for so long as monitoring of the heart's electrical activity is required. The template carries ten electrodes, the standard six precardial electrodes and four limb electrodes. A pair of defibrillation electrodes are incorporated into the template are also correctly located on the patient when the template is placed on the chest by its location tab.

10 Claims, 2 Drawing Sheets

DISPOSABLE ECG CHEST ELECTRODE TEMPLATE WITH BUILT-IN DEFIBRILLATION ELECTRODES

BACKGROUND OF THE INVENTION

1. Field of the Invention

The present invention relates generally to improvements in disposable electrode devices and more particularly pertains to a new and improved template for placing a plurality of electrodes on a patient's chest.

2. Description of Prior Art

An electrocardiogram (ECG) is a painless recording of the heart's electrical activity. This electrical activity is detected by small metal electrodes which are placed on the patient's chest and sometimes on the wrists and ankles. The electrical signals detected are carried from the electrodes through wires to an ECG machine. The ECG machine transforms the signals into standard patterns or waves. The different waves represent the different areas of a human heart through which tiny electrical currents flow, causing the heart to contract and relax. The P wave, for example, represents the current in the atria, or the upper chambers of the heart. The QRS complex represents the current in the ventricles. The T wave represents the heart's rest period as it repolarizes, or recharges electrically between heart beats.

The paper tracing of the ECG waves produced by the ECG machine shows not only the heart rate and heart rhythum, it can also give important clues about damage to the heart muscle or pericardium, the membrane around the heart. Furthermore, changes in ECG waves from one session to another may reflect the action of certain cardiac medications. ECG abnormalities may also indicate that a serious chemical imbalance exists in the blood which is affecting the heart's electrical activity. An ECG can distinguish between a heart attack that occurred in the past and one in progress at the time the ECG is being taken.

Besides obtaining the recording of the heart's electrical activity during rest, the more important ECG readings are taken while during exercise or while going about normal ambulatory activity. The exercise ECG records heart patterns while a person walks on a treadmill or pedals a stationary bicycle, for example. This technique is also called a stress test. This type of ECG is more likely to spot abnormal heart patterns, and an insufficient blood or oxygen supply to the heart muscle during exercise. Ambulatory ECG or Holter monitoring (ECH) records heart patterns usually over a 24-hour or longer period of time while a person goes about his daily activities. The standard Holter monitoring process requires that small electrodes that stick to the skin are connected to a portable recording device on a shoulder strap or belt worn under the patient's clothing. The recorded information can then later be analyzed by a computer and printed out much like a standard ECG. These ambulatory monitoring systems also can be used to transmit heart patterns to a hospital or doctor while a person is having symptoms. When a symptom develops while wearing the ECH, the patient simply dials a telephone number and transmits the readings from the Holter recorder over a telephone line.

The ECH systems are used generally to detect or monitor abnormal heart rhythms, or arrhythmias, which arise from problems with the electrical conduction system of the heart. Arrhythmias can occur anywhere in the atria or the ventricles of the heart. These arrhythmias can be either too slow or too fast. Abnormally slow rhythms sometimes results from slower firing of impulses, a condition called sinus bradycardia. An abnormally slow heart beat is dangerous. The heart does not pump enough blood to supply the brain and the rest of the body with oxygen. In such cases, episodes of dizziness, light headedness or fainting may occur.

Abnormally fast heart rhythms, such as for example, atrial fibrillation in which the atria contracts in a rapid uncoordinated manner, reduces the pumping efficiency of the heart. In a person with heart disease, the reduced pumping efficiency may lead to heart failure or stroke. Another more dangerous type of rapid arrhythmia is ventricular fibrillation in which ventricular contractions are rapid and chaotic. This fibrillation prevents the ventricles from pumping blood efficiently and can lead to death within minutes. Ventricular fibrillation is usually reversed with an electrical defibrillator, a device that delivers a shock to the heart. The shock briefly stops the heart from beating and when the heart beat starts again, the SA node is usually able to resume a normal beat.

The current standard method of obtaining ECG data requires the placement of up to ten single electrodes upon a patient's chest in order to monitor the heart rhythm and obtain the ECG tracings. The manual placement of these electrodes is tedious with technical error resulting in increased variance from monitor session to monitor session with decreased reproducible results. Moreover, these individual ECG electrodes are produced by a variety of manufacturers in different ways using different materials and styles and having different sensitivities.

There have been attempts in the prior art to provide a flexible sheet which carries a plurality of fixed electrodes positioned in a specific configuration which allows the placement of these plurality of electrodes on a patient's chest in a manner which provides consistency in the dimensional relationship between the electrodes on the flexible sheet. However, these prior art methods do not have any way of ensuring that the flexible sheet, with its plurality of electrodes, is placed in the correct position on the patient's chest every time.

SUMMARY OF THE INVENTION

The present invention permits quick, easy and correct placement of a ten electrode array carried by a flexible template to monitor the electrical activity of a patient's heart, by a locating tab on the template. A pair of defibrillation electrodes may also be located on the template ready for use, if necessary. The template and electrodes are x-ray invisible so that the template and electrodes need not be removed during diagnostic procedures. The template is adapted to connect to the three or four most popular monitoring and defibrillation machines used by paramedics and in hospital emergency rooms, critical care units, telemetry wards, outpatient Holter and Event monitors. The template also allows quick and accurate placement by the lay person in any setting. The template proves its critical worthiness when applied by the lay person during an out of hospital cardiac event when used in conjunction with an AED.

BRIEF DESCRIPTION OF THE DRAWINGS

The exact nature of this invention as well as its objects and advantages will become readily apparent from consideration of the following detailed description when considered in conjunction with the accompanying drawings, in which like reference numerals designate like parts throughout the figures thereof and wherein.

DESCRIPTION OF THE PREFERRED EMBODIMENTS

Figure 1:
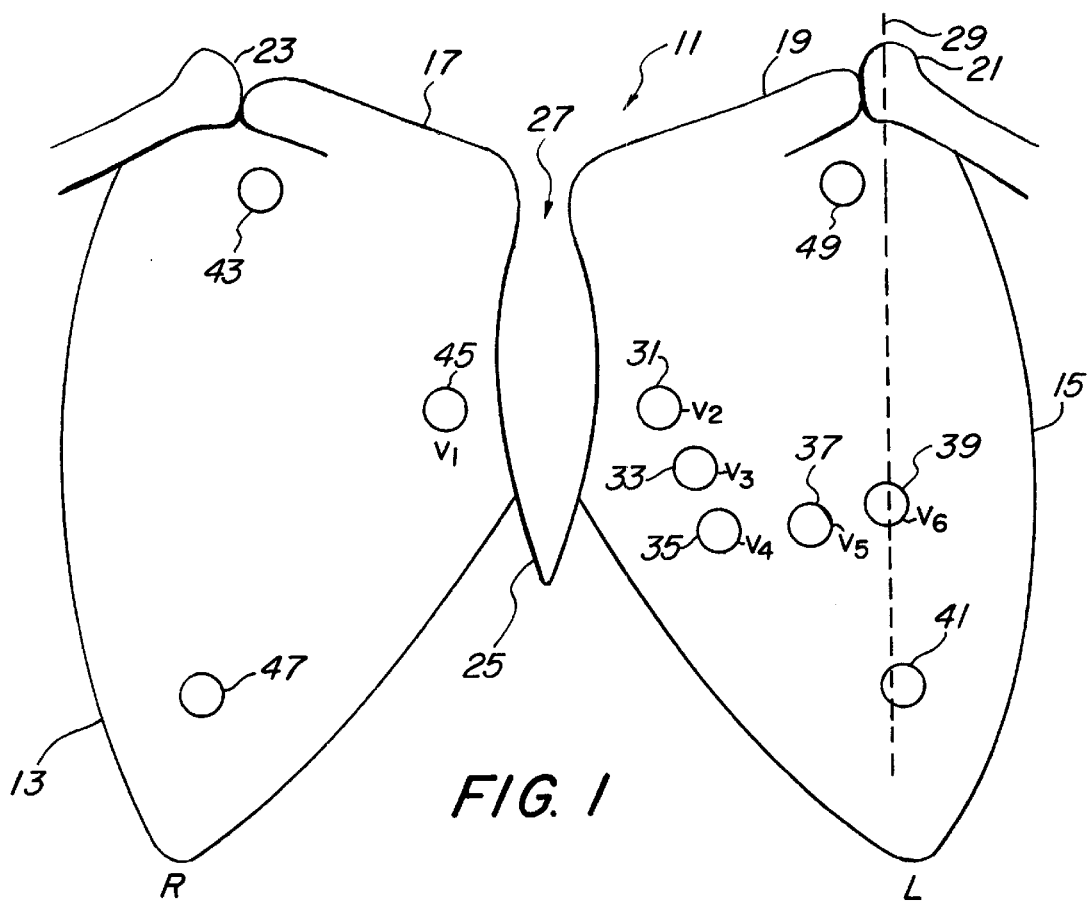
FIG. 1 is a schematic illustration of a human chest with individual electrodes located thereon.

FIG. 1 illustrates the chest 11 of a patient with the outline, for reference, of a left lung 15, the right lung 13, left clavicle 19, right clavicle 17, left shoulder bone 21, and the right shoulder bone 23. A constant point of reference on every patient's chest is the super sternal notch 27 and the mid-axillary line 29 at the right shoulder 21.

FIG. 1 illustrates the placement of ten electrodes, with seven electrodes located on the left side, and three located on the right side. The six main electrodes, 45, 31, 33, 35, 37 and 39, also known as the precordial electrodes, monitor activity in the heart's horizontal plane through the lateral and anteroseptal walls. These electrodes are all positive. A left shoulder electrode 49 is the negative electrode. When manually placing these electrodes, they are placed across the chest in successive steps starting from electrode 45 going left to electrode 39.

Electrode 45 is a positive electrode that is placed at about the fourth intercostal space to the right of the sternum 25. Electrode 31 is a positive electrode that is placed in the fourth intercostal space to the left of the sternum 25. Electrode 33 is a positive electrode that is placed between the fourth and the fifth intercostal spaces. Electrode 35 is a positive electrode that is placed at the fifth intercostal space in the midclavicular line (not shown). Electrode 37 is a positive electrode that is placed at the fifth intercostal space between the midclavicular and the mid-axillary line. Electrode 39 is a positive electrode that is placed in the fifth intercostal space in the mid-axillary line.

Electrodes 43, 47, 49, and 41 act as standard leads in the formulation of Einthoven's Triangle. The standard leads are bipolar leads because they are composed of two electrodes, one that is negative and one that is positive. The ECG records the difference in electrical potential between them.

Electrode 49 is placed at the left shoulder for the purpose of providing the positive lead in relationship to electrode 43. This relationship forms Lead I in Einthoven's Triangle. Electrode 49 also provides the negative lead in relationship to electrode 41. This relationship forms Lead III in Einthoven's Triangle. Electrode 41 is placed at the mid-axillary line on the inferior aspect of the left chest wall for the purpose of providing the positive lead in relationship to electrode 49. This relationship forms Lead III in Einthoven's Triangle. Electrode 41 also provides the positive lead in relationship to electrode 43. This relationship forms Lead II in Einthoven's Triangle. Electrode 43 is placed at the right shoulder for the purpose of providing the negative lead in relationship to electrode 49. This relationship forms Lead I in Einthoven's Triangle. Electrode 43 also provides the negative lead in relationship to electrode 41. This relationship forms Lead II in Einthoven's Triangle. Electrode 47 is placed at the mid-axillary line on the inferior aspect of the right chest wall for the purpose of stabilizing the ECG, but this electrode takes no part in lead information.

As FIG. 1 illustrates, the individual placement of these electrodes is tedious, time consuming, and complicated with respect to their correct location. The chances of the electrodes being incorrectly located in an emergency high-stress situation is more than probable.

Figure 2:
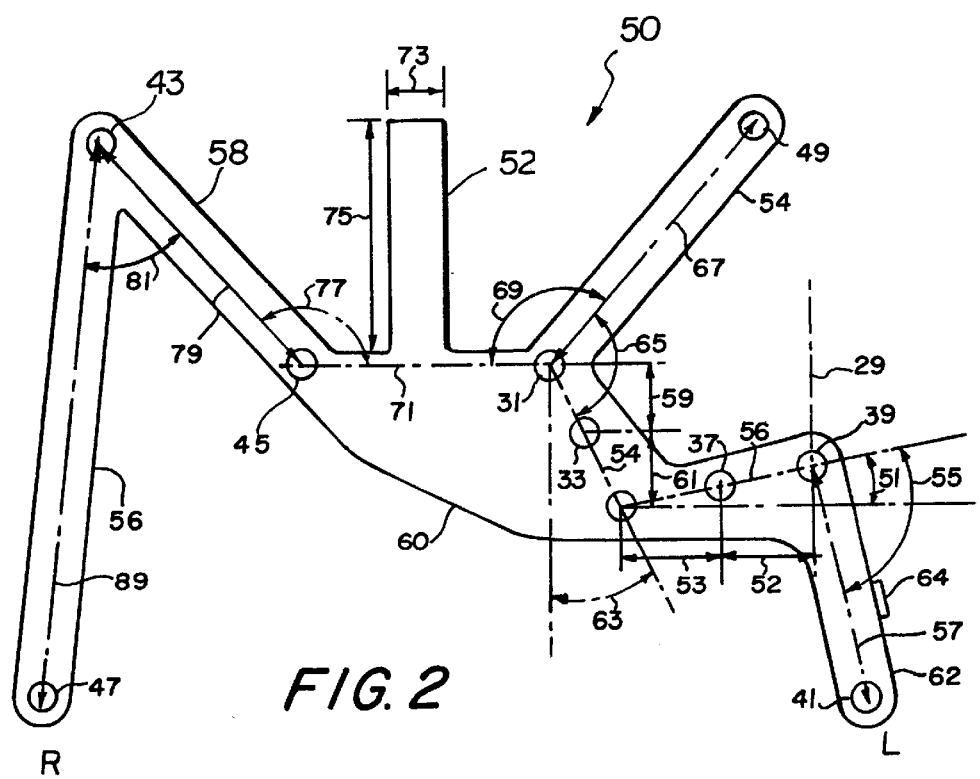
FIG. 2 is a schematic illustration of the template of the present invention.

FIG. 2 illustrates the template 50 of the present invention carrying the 10 electrodes 47, 43, 45, 31, 33, 35, 37, 39, 41, and 49 in the arrangement illustrated in FIG. 1. The spacing between each electrode and its placement with respect to the other is correct for the chest of an average sized human. The distances between the electrodes can be modified to accommodate a larger chest by increasing the distances between them, or a smaller chest by decreasing the distances between them. A larger template for large chests, and a smaller template for small chests is equally contemplated.

For medium sized chests as illustrated, the electrodes are laid out according to the following dimensions. The three electrodes 39, 37 and 35 lie on a line 56 that is at an angle 51 from a horizontal line. Angle 51 is approximately ten degrees (10°). Electrode 39 lies along the vertical mid-axillary line 29. Electrode 37 is spaced from electrode 39 on line 56 by distance 52 which is about six centimeters. Electrode 35 is spaced from electrode 37 by distance 53 which is about six centimeters. The bottom left side electrode 41 is on a line 57 spaced from electrode 39 by about ten centimeters. The line 57 is at an angle 55 from the line 56 of electrodes 39, 37 and 35. Angle 55 is about ninety degrees (90°). Electrodes 31, 33 and 35 lie on a line 54 which is at an angle 63 from a vertical line. Angle 63 is approximately forty degrees (40°). Electrode 33 is at a distance 61 from electrode 35, which is about 4 centimeters. Electrode 31 is at a distance 59 from electrode 33 which is about 4 centimeters. Left shoulder electrode 49 lies along a line 67 which is at an angle 65 from the line 54 of electrodes 31, 33, and 35. Angle 65 is about ninety degrees (90°). The distance between electrode 49 and electrode 31 is approximately 14 centimeters. In this manner, the seven electrodes on the left side of the chest are accurately located with respect to each other for a medium or average size chest.

On the right side of the chest, electrode 45 lies along a horizontal line 71 at 12 centimeters from electrode 31. Right shoulder electrode 43 lies on a line 79 which is at an angle 77 from horizontal line 71 of electrode 45. Angle 77 is approximately one hundred and thirty-five degrees (135°). The distance between electrode 43 and electrode 45 is approximately 13 ½ centimeters. The bottom right chest electrode 47 lies along a line 89 that is at an angle 81 from line 79 of electrode 43. The angle 81 between lines 79 and 89 is about seventy degrees (70°). The distance between electrode 47 and electrode 43 is about 18 centimeters. In this manner, the right side three electrodes are accurately located with respect to each other for a medium or average size chest. These ten electrodes are fixed to the template and thereby retain their spatial relationship.

In order to enable the correct placement of the template 50 on the chest of a patient, the template includes a tab 52 which has a certain length 75 which is approximately ten (10) centimeters and a certain width 73, approximately four (4) centimeters. The length of the tab 75 is determined for the average size chest. The tab is designed to be easily removed by the patient if the template is to be used on a long-term basis.

The template is preferably made up of a pad of an electrically conductive gel such as Ludlow Tech Corp. Promeon RG73P, electrically insulative and x-ray transparent PB foam, and a removable carrier sheet, such as PTFE. The electrodes may be made of silver/silver chloride metal which are embedded in the pad. Conduction conduits or wires (not shown) made of x-ray transparent metal coated carbon fiber such as produced by Amoco Performance Products, Inc. of Atlanta, Ga. and more specifically described in U.S. Pat. No. 3,677,705, or conductive channels of graphite filled polyvinyl chloride film, known as "Conduction," and available from Burkhardt/Freeman, Holyoke, Mass. or from Prime Label and Screen, Inc. of New Berlin, Wis. are used to connect each of the electrodes to a connection point 64 on the template 50. External wires are connected to the internal conduction conduits (not shown) by conductive tabs 64. It is contemplated that a variety of adaptors between the conductor tab 64 and the major pre-hospital and in-hospital cardiac monitor units available today would be part of a kit that includes this ECG electrode template 50.

Figure 3:
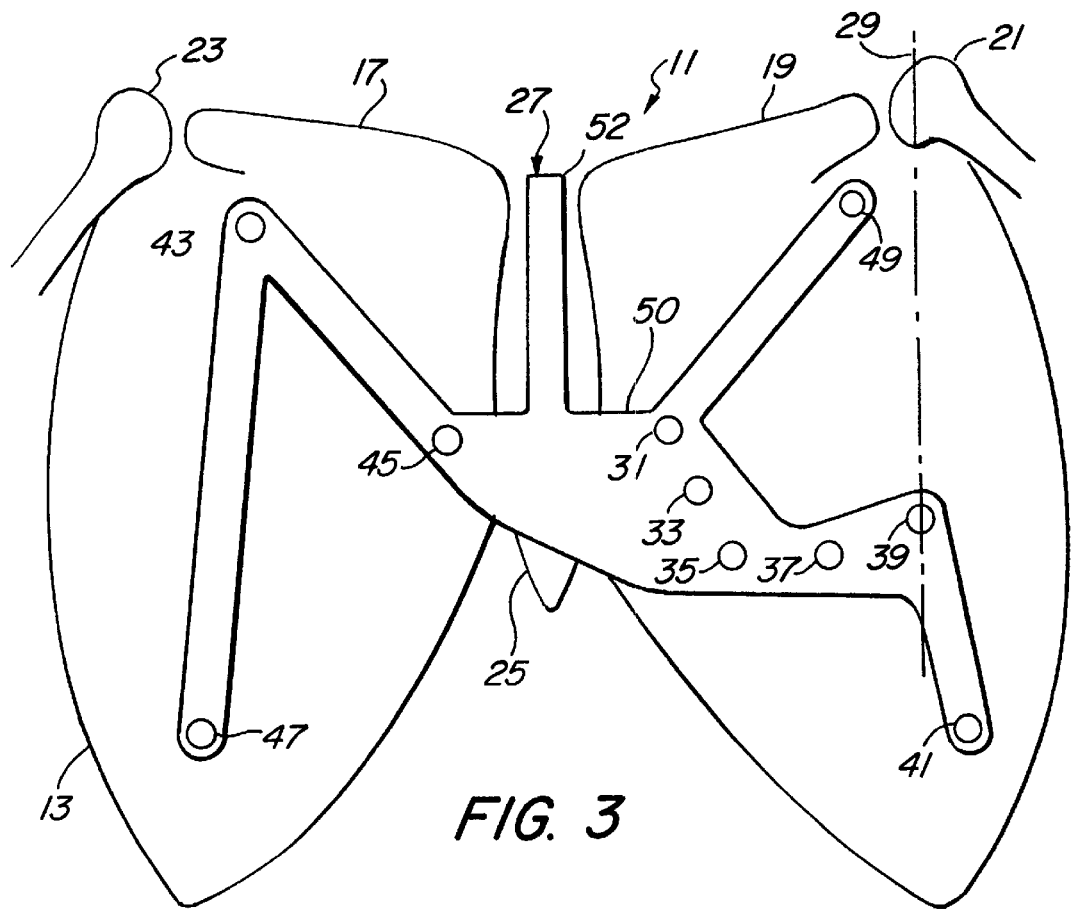
FIG. 3 is a schematic illustration of a human chest with the template of the present invention located thereon.

The ECG template 50 is quickly and correctly located on the chest 11 of a patient, as shown in FIG. 3, by placing the top of the tab 52 at the supra sternal notch 27 and the left most precordial electrode 39 on the vertical mid-axillary line 29, which drops straight down from the shoulder. Once these two points are located, the entire template 50 is smoothed across the chest of the patient on its left and right side, thereby completely locating all ten electrodes.

Figure 4:
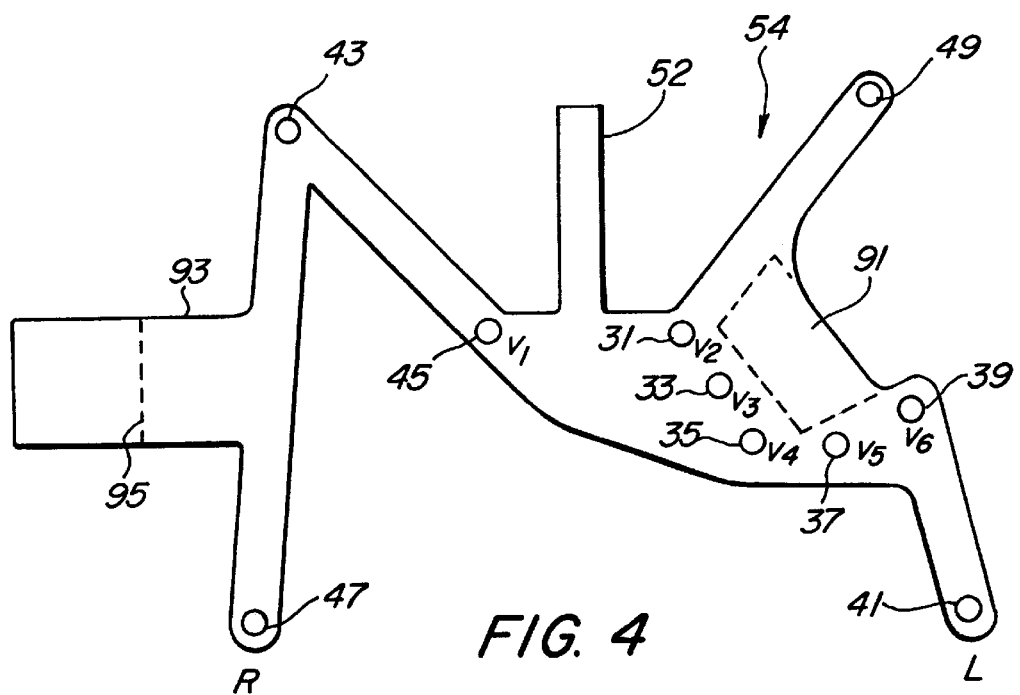
FIG. 4 is a schematic illustration of an alternate embodiment of the template of the present invention.

In acute response situations where a patient is in great difficulty, it sometimes becomes necessary to defibrillate the patient. The monitoring electrodes on a patient's chest would have to be removed before defibrillation. The alternate embodiment of the template 54 shown in FIG. 4 includes a pair of defibrillation electrodes 91 and 93 located in the template 54 in relation to the electrodes as shown. The area of electrode 91, plus the area of electrode 93, total the required defibrillation surface area of 150 centimeters. Electrode 93 is placed in the right infra-scapular region of the patient's chest. Electrode 91 is placed on the left side, close to the mid-axillary line. These defibrillation electrodes 91 and 93 are also x-ray invisible. Conductors that may or may not be x-ray invisible (not shown) would lead from the defibrillation electrodes to a connection point (not shown) for connection to a standard defibrillation machine.

What is claimed is:

1. A disposable electrocardiogram electrode template for simultaneously, quickly and correctly placing a plurality of sensors on a human chest, the template comprising:

a flexible sheet of predetermined size and shape having a tab extending from the top of the flexible sheet for a predefined length, the sheet being made of a pad of hypoallergenic hydrogel, an x-ray transparent PB foam, and a removable carrier sheet; and a plurality of electrode sensors embedded in the pad at predetermined fixed locations on the pad, each electrode sensor being an x-ray transparent metal contact;

whereby the plurality of electrode sensors can be quickly and correctly located on the human chest by aligning the sheet on the chest with the tab aligned on a vertical line and the top of the tab located at the supra sternal notch.

2. The electrode template of claim 1 wherein the plurality of sensors comprises ten electrodes.

3. The electrode template of claim 1 further comprising: conductive tabs on an edge of the pad for connecting to x-ray transparent wires that electrically connect each one of the metal contact sensors to the conductive tabs.

4. The electrode template of claim 3 further comprising first and second defibrillation electrodes located at predetermined fixed locations on the pad.

5. The electrode template of claim 1 further comprising first and second defibrillation electrodes located at predetermined fixed locations on the pad.

6. The template of claim 5 wherein the first defibrillation electrode is located above a precordial electrode sensor in the pad adapted to be close to the midaxillary line.

7. The template of claim 6 wherein the second defibrillation electrode is located between a right shoulder and right chest electrode sensors in the pad adapted to be in the right infra-scapular region of the chest.

8. A disposable electrocardiogram electrode template for simultaneously, quickly and correctly placing electrode sensors on a human chest, the template comprising:

a pad made of hypoallergenic hydrogel, an x-ray transparent PE foam, and a removable carrier sheet, the pad having a tab with a predefined length extending from a top side; and ten x-ray transparent electrode sensors embedded in the pad so that on the left side of the pad, electrode sensors one, two and three lie on a line that is at an angle from a horizontal, with one of the three electrode sensors lying along a vertical midaxillary line when the template is placed on the chest, a fourth electrode sensor lies below the electrode sensors one, two and three on a line that is perpendicular to the line of the electrode sensors one, two and three, a fifth and sixth electrode sensor lie on a line at an angle to a vertical above electrode sensors one, two and three, a seventh electrode lies above electrode five and six on a line perpendicular to the line for electrode sensors five and six, on the right side of the pad, an eighth electrode sensor lies on a horizontal line, a ninth electrode sensor lies above the eighth electrode sensor on a line at an angle greater than ninety degrees to the line of the eighth electrode sensor, a tenth electrode sensor lies below the eighth electrode sensor on a line less than ninety degrees to the line of the ninth electrode sensor;

whereby the ten electrode sensors can be quickly and correctly located on the human chest by aligning the pad on the chest so that the tab on the top of the pad is aligned with a vertical mid-auxiliary line and the top of the tab is located at the supra sternal notch.

9. The template of claim 8 where a first defibrillation electrode is located above the first, second and third electrode sensors in the pad close to the midaxillary line.

10. The template of claim 9 where a second defibrillation electrode is located between the ninth and tenth electrode sensors in the pad.

* * * * *